United States Patent [19]

Katsumata et al.

[11] Patent Number: 4,617,267

[45] Date of Patent: Oct. 14, 1986

[54] PLASMID PCG1 FROM CORYNEBACTERIUM GLUTAMICUM

[75] Inventors: Ryoichi Katsumata, Machida; Akira Furuya, Kawasaki, both of Japan

[73] Assignee: Kyowa Hakko Kogyo Co., Ltd., Tokyo, Japan

[21] Appl. No.: 573,591

[22] Filed: Jan. 25, 1984

Related U.S. Application Data

[63] Continuation-in-part of Ser. No. 346,867, Feb. 8, 1982, abandoned.

[30] Foreign Application Priority Data

Feb. 12, 1981 [JP] Japan ................................. 56-18101

[51] Int. Cl.⁴ ..................... C12P 19/34; C12N 1/20; C12N 1/00; C12N 15/00
[52] U.S. Cl. .................................. 435/91; 435/253; 435/172.3; 935/29; 935/72
[58] Field of Search ............... 435/110, 111, 112, 317, 435/172.3, 253, 91, 320; 935/29, 72

[56] References Cited

U.S. PATENT DOCUMENTS

| | | | |
|---|---|---|---|
| 3,002,889 | 10/1961 | Kinoshita et al. | 435/111 |
| 3,003,925 | 10/1961 | Kinoshita et al. | 435/110 |
| 3,220,929 | 11/1965 | Kinoshita et al. | 435/110 |
| 4,500,640 | 2/1985 | Katsumata et al. | 435/253 |

OTHER PUBLICATIONS

Humphreys et al, Biochimica et Biophysica Acta, vol. 383, pp. 457–463 (1975).

*Primary Examiner*—Alvin E. Tanenholtz
*Attorney, Agent, or Firm*—Fitzpatrick, Cella, Harper & Scinto

[57] ABSTRACT

Disclosed is a novel vector, plasmid pCG1, and a process of producing plasmid pCG1 from *Corynebacterium glutamicum.*

6 Claims, No Drawings

PLASMID PCG1 FROM *CORYNEBACTERIUM GLUTAMICUM*

This application is a continuation-in-part of application Ser. No. 346,867 filed Feb. 8, 1982, now abandoned.

BACKGROUND OF THE INVENTION

The present invention relates to a novel isolated plasmid, plasmid pCG1, and a process for producing the same.

The role of vectors in gene engineering is stated clearly in *Recombinant Molecules*: Impact on Science and Society, Miles International Symposium Series No. 10, edited by R. F. Beers and E. G. Basset, Raven Press, New York. The usefulness of plasmids as vectors in gene engineering is recognized on the host-vector system of *Escherichia coli*. Recombinant DNA technology has also been developed on industrially useful microorganisms other than *Escherichia coli*, such as amylase-producing *Bacillus subtilis*, antibiotics-producing Actinomycetes and brewing alcohol-producing yeasts. Since vectors are essential for recombinant DNA technology, plasmids and phages have been searched for in these microorganisms.

Microorganisms belonging to *Corynebacterium glutamicum* or analogous species thereof are used in industrial production of useful substances such as glutamic acid, lysine and the like. A plasmid, or phage, useful as a vector in the microorganisms belonging to the genus Corynebacterium is essential to establish recombinant DNA technology on these microorganisms. Heretofore, a plasmid which is autonomously replicated in microorganisms belonging to the genus Corynebacterium has not been known.

SUMMARY OF THE INVENTION

In accordance with the present invention, plasmid pCG1 is produced from *Corynebacterium glutamicum* 225-57. The process for producing plasmid pCG1 comprises culturing *Corynebacterium glutamicum* 225-57 in a nutrient medium, disrupting the cultured cells, and recovering plasmid pCG1 from the disrupted cells. Plasmid pCG1 thus produced has been found to be useful as a vector to establish recombinant DNA technology on microorganisms belonging to the genus Corynebacterium.

Plasmid pCG1 is characterized by a molecular weight of about 2 megadaltons and the following cleavage sites for restriction endonucleases:

| Restriction enzyme | Number of cleavage sites |
| --- | --- |
| EcoRI | 1 |
| HindIII | 2 |
| HincII | 2 |
| BamHI | 0 |
| PstI | 0 |
| SalI | 0 |
| KpnI | 0 |

Microorganisms belonging to *Corynebacterium glutamicum*, and especially the strain *Corynebacterium glutamicum* 225-57 ATCC 31808, carries plasmid pCG1. In another embodiment of the invention, plasmid pCG1 isolated from *Corynebacterium glutamicum* 225-57 is inserted into a microorganism other than 225-57 belonging to the genus Corynebacterium.

DETAILED DESCRIPTION OF THE INVENTION

Plasmid pCG1 has a molecular weight of about 2 megadaltons and the restricted cleavage sites mentioned below for several conventional restriction endonucleases. The properties show that plasmid pCG1 is useful as a cloning vector in microorganisms belonging to *Corynebacterium glutamicum* and analogous species thereof and as a reagent for the study of recombinant DNA technology because an objective gene can be inserted in the plasmid and the inserted plasmid is autonomously replicated in the microorganisms.

Plasmid pCG1 is produced from the novel 225-57 strain which has been recently isolated from soil. Taxonomic studies of the 225-57 strain were carried out according to the description in *Manual of Microbiological Methods* by the Society of American Bacteriologist Committee on Bacteriological Technique (1957).

The properties of the 225-57 strain are set forth below:

I. Morphological characteristics of cells of the 225-57 strain:

Usually ellipsoidal or short rods 0.7–1.0 by 1.0–3.0μ; Pleomorphic due to snapping division and branching cells; Gram positive; Non-motile; Non-spore-forming.

II. Culture characteristics on a rich nutrient medium:

On an agar plate, a single, circular, dull, rough and pale yellow colony; on a slant, a similar pale yellow opaque colony; on an agar stab, abundant growth on surface and weak growth in deep; in a liquid medium, slight growth and slightly flocculent sediment.

III. Physiological characteristics:

| | | |
| --- | --- | --- |
| (1) | Temperature: | optimum temperature 25–37° C.; growth occurs slightly at 42° C. |
| (2) | pH: | optimum pH 7–8; growth occurs at pH 6–9 |
| (3) | Thermal resistance: | none |
| (4) | Relation to free oxygen: | aerobic |
| (5) | Gelatin liquefaction: | none |
| (6) | Metabolism of casein: | negative |
| (7) | Indole production: | none |
| (8) | Catalase: | positive |
| (9) | Assimilation of starch: | negative |
| (10) | Acid production from glucose, fructose, mannose and maltose; non-acid production from xylose, galactose, lactose and glycerol | |
| (11) | Requirement of biotin: | positive |
| (12) | Glutamic acid is accumulated in a large quantity in a medium wherein the amount of biotin is restricted. | |
| (13) | Lactic acid and α-ketoglutaric acid are accumulated in a medium containing biotin in a high concentration. | |

These characteristics were compared with those of bacteria disclosed in J. Gen. Appl. Microbiol., 73, 279–301 (1967). Since the characteristics coincide well with those of *Corynebacterium glutamicum* except for the slight difference in the property of the surface of a single colony, the 225-57 strain is identified as *Corynebacterium glutamicum*. This novel strain has been deposited with the Fermentation Research Institute, Agency of Industrial Science and Technology, Japan, under accession number FERM-P 5865 and with the American Type Culture Collection, Rockville, Md., USA, under accession number ATCC 31808.

In order to produce plasmid pCG1 from the cells of *Corynebacterium glutamicum* 225-57, the cultured cells have to be disrupted. Since cells of microorganisms belonging to the genus Corynebacterium or analogous species thereof when cultivated in a conventional medium are insensitive to a bacteriolytic enzyme such as egg white lysozyme, it is necessary to render them sensitive to such lysozyme prior to use.

To render *Corynebacterium glutamicum* 225-57 sensitive to lysozyme, a method is employed which is used for *Brevibacterium lactofermentum* [Japanese Published Unexamined Patent Application No. 28896/79] which is analogous to *Corynebacterium glutamicum;* or for *Streptococcus faecalis* [Can. J. Microbiol., 7, 363-373 (1961)] which is gram-positive and insensitive to egg white lysozyme like *Corynebacterium glutamicum*. According to this method, during the log phase cultivation period, penicillin in an amount which does not inhibit or sub-inhibit the growth, usually 0.1-10 U/ml culture liquor, is added to the medium and cultivation is continued for several generations. Lysozyme-sensitive cells are thus obtained.

For culturing, a liquid medium and cultivation methods which are usually used for culturing microorganisms belonging to *Corynebacterium glutamicum* and analogous species thereof are employed. The cell walls of cultured cells of *Corynebacterium glutamicum* 225-57 which are treated with penicillin mentioned above are easily disrupted with lysozyme. Plasmid pCG1 thus can be condensed and isolated from the disrupted cells by a conventional method such as disclosed in Biochim. Biophys. Acta, 383, 457-463 (1975).

The plasmid pCG1 thus obtained is a deoxyribonucleic acid with a molecular weight of about 2 megadaltons. Plasmid pCG1 has the following cleavage sites for the following restriction endonucleases:

| Enzyme | Number of cleavage sites |
|---|---|
| EcoRI | 1 |
| HindIII | 2 |
| HincII | 2 |
| BamHI | 0 |
| PstI | 0 |
| SalI | 0 |
| KpnI | 0 |

The name of the enzymes are abbreviations of the restriction endonucleases obtained from the following microorganisms:

| EcoRI | *Escherichia coli* |
| HindIII | *Haemophilus influenzae* |
| HincII | *Haemophilus influenzae* |
| BamHI | *Bacillus amyloliquefacience* |
| PstI | *Providencia stuartii* |
| SalI | *Streptomyces albus* |
| KpnI | *Klebsiella pneumoniae* |

Kpn I is a product of Bethesda Research Laboratories and the others are products of Takara Shuzo Co., Ltd.

The number of cleavage sites for restriction endonucleases are determined by completely digesting plasmid pCG1 in the presence of an excess amount of restriction endonucleases, subjecting the digest to 0.8% agalose gel electrophoresis, and thereafter counting the number of isolated fragments. The molecular weight is determined by measuring the molecular weight of each fragment in the digested plasmid pCG1 based on the standard curve plotted with electrophoretic distances on agalose gel electrophoresis for the fragments obtained by digesting λ phage DNA of *Escherichia coli* with HindIII [J. Mol. Biol., 98, 551-564 (1975)] and in the case of plural fragments, summing up the molecular weights.

Plasmid pCG1 is useful because it is autonomously replicated in industrially important microorganisms belonging to *Corynebacterium glutamicum* and analogous species thereof which are used for the production of useful substances such as amino acids, nucleic acids, and the like. Plasmid pCG1, therefore, can be used as a cloning vector in these host microorganisms. Accordingly, it is possible to get a gene relating to bio-synthesis or regulation of useful substances such as amino acids, nucleic acids, and the like from the microorganisms belonging to *Corynebacterium glutamicum* and analogous species thereof or others; and using the plasmid pCG1, it is then possible to clone that gene in the microorganisms belonging to the genus Corynebacterium or analogous species thereof by conventional in vitro recombinant DNA technology. Moreover, the present invention provides a process which increases the productivity of the useful substances by the stimulation of a biosynthetic system based on the amplification of the cloned genetic information.

Since it is apparent that a part of the plasmid functions to replicate plasmid pCG1 autonomously, derivatives of plasmid pCG1, for example a plasmid wherein a region of plasmid pCG1 is deleted or a plasmid wherein another DNA fragment is inserted in plasmid pCG1, may be replicated autonomously. Therefore, it is clear that the DNA obtained by the modification of plasmid pCG1 is useful as well as plasmid pCG1 itself.

As an illustration of the present invention an example is set forth below.

EXAMPLE 1

(1) Isolation of plasmid pCG1 from the cultured cells of *Corynebacterium glutamicum* 225-57:

*Corynebacterium glutamicum* 225-57 is cultured with shaking in an NB medium consisting of 20 g of powdered bouillon, 5 g of yeast extract and 1 l of pure water and adjusted to pH 7.2 at 30° C. for 18 hours. Then, 5 ml of the seed culture is inoculated into 400 ml of a semi-synthetic medium consisting of 20 g of glucose, 10 g of $(NH_4)_2SO_4$, 3 g of urea, 1 g of yeast extract, 1 g of $KH_2PO_4$, 0.4 g of $MgCl_2.6H_2O$, 10 mg of $FeSO_4.7H_2O$, 0.2 mg of $MnSO_4.(4-6)H_2O$, 0.9 mg of $ZnSO_4.7H_2O$, 0.4 mg of $CuSO_4.5H_2O$, 0.09 mg of $Na_2B_4O_7.10H_2O$, 0.04 mg of $(NH_4)_6Mo_7O_{24}.4H_2O$, 30 μg of biotin, 1 mg of thiamine hydrochloride and 1 l of pure water and the inoculated medium is adjusted to pH 7.2. Culturing is carried out with shaking at 30° C. Optical density (OD) at 660 nm is measured by a Tokyo Koden colorimeter and, at the OD value of 0.2, penicillin G is added to the broth to a final concentration of 0.5 U/ml. Cultivation is continued at 30° C. to an OD value of about 0.6.

Cells are recovered from the culture broth; washed with TES buffer solution (pH 8.0) consisting of (i) 0.03M tris(hydroxymethyl)aminomethane (Tris), (ii) 0.005M EDTA and (iii) 0.05M NaCl and thereafter suspended in a lysozyme solution (pH 8.0) consisting of 25% sucrose, 0.1M NaCl, 0.05M Tris and 0.8 mg/ml lysozyme to make 20 ml of a suspension. The suspension is allowed to react at 37° C. for 4 hours. Then, 2.4 ml of 5M NaCl, 0.6 ml of 0.5M EDTA (pH 8.5) and 4.4 ml of a mixed solution of 4% sodium laurylsulfate and 0.7M NaCl are added successively to the reaction suspension. The mixture is stirred slowly and put on an ice water bath for 15 hours.

Whole lysate is put into a centrifugation tube and centrifuged under 69,400×g at 4° C. for 60 minutes to obtain a supernatant. To the supernatant is added 10% by weight of polyethyleneglycol 6,000. The mixture is stirred slowly to provide a uniform blend and subjected to an ice water bath. After 16 hours, the mixture is subjected to centrifugation under 1,500×g for 10 minutes to obtain a pellet. The pellet is redissolved in 5 ml of TES buffer solution and 2.0 ml of 1.5 mg/ml ethidium bromide is added. To the mixture is added cesium chloride. After dissolving, the density is adjusted to 1.580. The solution is subjected to centrifugation under 105,000×g at 180° C. for 48 hours.

After the density gradient centrifugation, a circular DNA closed with a covalent bond is found as a high density band located in the lower part of the centrifugation tube by ultraviolet irradiation. The band is taken out from the side of the tube with an injector to obtain a fraction containing plasmid pCG1. The fraction is treated five times with equal amount of isopropylalcohol solution consisting of 90% by volume of isopropylalcohol and 10% TES buffer solution containing saturated amount of cesium chloride to remove ethidium bromide. Then, the residue is subjected to dialysis with TES buffer solution.

To 1 ml of the thus obtained dialysate containing plasmid pCG1 is added 2 ml of ethanol. A precipitate deposits. The deposited precipitate is recovered by centrifugation and dried in vacuo at $-20°$ C. to obtain 50 $\mu$g of plasmid pCG1.

(2) Cleavage specificity with various restriction endonucleases and molecular weight of plasmid pCG1:

In this step, 0.5 $\mu$g of plasmid pCG1 prepared above is dissolved in 10 $\mu$l of TES buffer solution (pH 8.0) and two folds or more restriction endonucleases such as EcoRI, HindIII, BamHI, PstI, Sal I, Hinc II and Kpn I is added under the suitable conditions for each restriction endonuclease. The digested specimen is provided to horizontal 0.8% agalose gel containing 0.6 $\mu$g/ml ethidium bromide and electrophoresis is carried out at a constant additional voltage of 7 V per 1 cm in width for 3–4 hours. The number of fragments formed is counted by ultraviolet irradiation on the gel plate. The molecular weight of each fragment is determined from the electrophoretic distance and that of plasmid pCG1 is determined by summing them up. The molecular weight of plasmid pCG1 is determined by reference to a standard curve plotted with electrophoretic distance of each DNA fragment, the molecular weight of which is already known. The DNA fragments are produced by the digestion of λ phage DNA with HindIII and subjected to electrophoresis on the same agalose gel as that for plasmid pCG1. The results are illustrated in the following table.

| Enzyme | Number of cleavage sites | Molecular weight of each fragment (Megadalton) | Molecular weight of pCG1 by summing up (Megadalton) |
|---|---|---|---|
| EcoRI | 1 | 2.0 | 2.0 |
| HindIII | 2 | 1.73, 0.27 | 2.0 |
| HincII | 2 | 1.50, 0.50 | 2.0 |
| BamHI | 0 | — | — |
| PstI | 0 | — | — |
| SalI | 0 | — | — |
| KpnI | 0 | — | — |

EXAMPLE 2

In this example, a functional derivative of plasmid pCG1 is constructed. Plasmid pCG1 is first isolated from *Corynebacterium glutamicum* 225-57 as in Example 1. Plasmid pCG4 is then isolated from *Corynebacterium glutamicum* 225-250 (ATCC 31830) following the same procedure as in Example 1. Plasmid pCG4 is characterized by a molecular weight of about 19 megadaltons, cleavage sites for the restriction endonucleases, Eco RI, Bam HI, Hind III, Pst I and Sal I of 4, 7, 9, 6 and 6 respectively and carries a gene for resistance to streptomycin and spectinomycin. Plasmid pCG1 is completely digested with Bgl II which is a restriction endonuclease derived from *Bacillus globigii* and is a product of Takara Shuzo Co., and plasmid pCG4 is completely digested with Bam HI which is a restriction endonuclease produced by Takara Shuzo Co., under suitable conditions for these restriction endonucleases. Then, 0.2 ml of a reaction solution (pH 7.6) consisting of 66 mM Tris-hydrochloride, 6.6 mM MgCl$_2$, 10 mM dithiothreitol, 0.5 mM ATP and 0.5 $\mu$g of each of the digested DNA is mixed with 0.1 U of T4 phage DNA ligase (product of Takara Shuzo Co.). The mixture is allowed to react at 4° C. overnight. Protoplasts of *Corynebacterium glutamicum* LA 103 strain are transformed by conventional procedure using 0.1 of the ligase reaction solution.

Isolation of transformants is carried out by conventional techniques using successive replication on NB agar medium containing 12.5 mg/ml of streptomycin and 100 mg/ml of spectinomycin respectively.

One of the thus obtained streptomycin resistant strains is treated as in Example 1 except that the addition of penicillin G during culturing is omitted to obtain 50 $\mu$g of a plasmid DNA. The plasmid DNA is digested with restriction endonucleases solely or in combination. The DNA fragments formed are analyzed by agarose gel electrophoresis as in Example 1 to determine the molecular weights and cleavage sites for restriction endonucleases. The thus obtained plasmid, named pCG11, has a molecular weight of about 4.5 megadalton and has cleavage sites for the restriction endonucleases, Eco RI, Pst I, Bgl II and Hinc II which is derived from *Haemophilus influenzae*.

*Corynebacterium glutamicum* LA 103 is then transformed with plasmid pCG11 to obtain a spectinomycin resistant transformant. The transformant harbors a plasmid having the same cleavage sites for restriction endonucleases as those of pCG11.

What is claimed is:

1. An isolated plasmid pCG1 characterized by a molecular weight of about 2 megadaltons and the following cleavage sites for restriction endonucleases:

| Restriction enzyme | Number of cleavage sites |
|---|---|
| EcoRI | 1 |
| HindIII | 2 |

-continued

| Restriction enzyme | Number of cleavage sites |
| --- | --- |
| HincII | 2 |
| BamHI | 0 |
| PstI | 0 |
| SalI | 0 |
| KpnI | 0 |

2. A process for producing plasmid pCG1 which comprises culturing *Corynebacterium glutamicum* 225-57 having the identifying characteristics of ATCC 31808 in a nutrient medium, disrupting the cultured cells and recovering plasmid pCG1 from the disrupted cells.

3. A biologically pure culture of *Corynebacterium glutamicum* having the identifying characteristics of ATCC 31808 from which plasmid pCG1 is recoverable.

4. A recombinant plasmid capable of autonomous replication in Corynebacterium constructed from the plasmid pCG1 defined in claim 1 by adding a foreign DNA fragment thereto.

5. A recombinant plasmid capable of autonomous replication in Corynebacterium constructed from the plasmid pCG1 defined in claim 1 by deleting a DNA region that does not affect its function to replicate autonomously and adding a foreign DNA fragment to said plasmid.

6. A biologically pure culture of a microorganism belonging to *Corynebacterium glutamicum* and harboring plasmid pCG1 or a recombinant plasmid as defined in claim 4 or 5.

* * * * *